(12) United States Patent
Wu et al.

(10) Patent No.: US 10,441,260 B2
(45) Date of Patent: Oct. 15, 2019

(54) EXPANDER

(71) Applicants: MEGAFORCE COMPANY LIMITED, New Taipei (TW); MacKay Memorial Hospital, Taipei (TW)

(72) Inventors: Wen-Chieh Wu, New Taipei (TW); Shu-Fen Chen, Taipei (TW); Pei-Yi Lee, Taipei (TW)

(73) Assignees: Megaforce Company Limited, New Taipei (TW); Mackay Memorial Hospital, Taipei (TW)

( * ) Notice: Subject to any disclaimer, the term of this patent is extended or adjusted under 35 U.S.C. 154(b) by 246 days.

(21) Appl. No.: 15/450,992

(22) Filed: Mar. 6, 2017

(65) Prior Publication Data

US 2017/0273550 A1 Sep. 28, 2017

(30) Foreign Application Priority Data

Mar. 28, 2016 (TW) .............................. 105109770 A

(51) Int. Cl.
| | |
|---|---|
| *A61B 17/02* | (2006.01) |
| *A61B 17/00* | (2006.01) |
| *A61B 90/00* | (2016.01) |
| *A61B 90/30* | (2016.01) |

(52) U.S. Cl.
CPC .... *A61B 17/02* (2013.01); *A61B 2017/00407* (2013.01); *A61B 2090/067* (2016.02); *A61B 2090/0811* (2016.02); *A61B 2090/309* (2016.02)

(58) Field of Classification Search
CPC .. A61B 1/24; A61B 1/32; A61B 17/02; A61B 17/0218
See application file for complete search history.

(56) References Cited

U.S. PATENT DOCUMENTS

| | | | | |
|---|---|---|---|---|
| 1,025,265 | A | * | 5/1912 | Grindle .............. A61B 17/0206 600/219 |
| 1,137,585 | A | * | 4/1915 | Craig, Jr. ................. A61C 5/90 433/140 |
| 1,437,995 | A | * | 12/1922 | Richter .................... A61B 1/24 600/219 |
| 1,843,221 | A | * | 2/1932 | Hanson .................. A61D 15/00 600/244 |
| 2,075,534 | A | * | 3/1937 | McCormack ............ A61B 1/24 600/219 |
| 2,481,007 | A | * | 9/1949 | Dugdale ................ A01K 97/18 43/53.5 |

(Continued)

*Primary Examiner* — Eric S Gibson

(74) *Attorney, Agent, or Firm* — Muncy, Geissler, Olds & Lowe, P.C.

(57) ABSTRACT

An expander includes a first handle, a second handle, a first supporting member, and a second supporting member. The first handle includes a first gripping portion, a first pivoting portion, a first connecting portion, and an expanding compass. The second handle includes a second gripping portion, a second pivoting portion, and a second connecting portion. The second gripping portion includes a thru groove, and the expanding compass passes through the thru groove. The second pivoting portion is pivoted to the first pivoting portion. The second connecting portion and the second gripping portion are extending from two ends of the second pivoting portion, and the extension direction of the second connecting portion is not parallel to the extension direction of the second gripping portion.

10 Claims, 6 Drawing Sheets

(56) References Cited

U.S. PATENT DOCUMENTS

| | | | | |
|---|---|---|---|---|
| 3,038,467 A * | 6/1962 | Sovatkin | A61B 17/0206 | 600/217 |
| 3,470,872 A * | 10/1969 | Grieshaber | A61B 17/0206 | 29/239 |
| 4,034,746 A * | 7/1977 | Williams | A61B 17/0206 | 600/217 |
| 4,356,821 A * | 11/1982 | Rind | A61M 16/0488 | 128/207.14 |
| 4,754,746 A * | 7/1988 | Cox | A61B 17/0206 | 600/210 |
| 4,896,661 A * | 1/1990 | Bogert | A61B 17/2812 | 600/219 |
| 4,991,566 A * | 2/1991 | Shulman | A61B 1/24 | 433/7 |
| 5,097,820 A * | 3/1992 | Shulman | A61B 1/24 | 600/237 |
| 5,462,435 A * | 10/1995 | Young | A61B 1/24 | 433/140 |
| 5,498,231 A * | 3/1996 | Franicevic | A61B 1/267 | 128/200.26 |
| 5,733,121 A * | 3/1998 | Goode | A61B 17/0206 | 433/140 |
| 5,843,125 A * | 12/1998 | Jempolsky | A61B 17/08 | 606/218 |
| 6,558,392 B1 * | 5/2003 | Martini | A61B 17/025 | 433/140 |
| 6,663,562 B2 * | 12/2003 | Chang | A61B 17/0206 | 600/213 |
| 2004/0024291 A1 * | 2/2004 | Zinkel | A61B 17/0206 | 600/218 |
| 2005/0027170 A1 * | 2/2005 | Nohara | A61B 17/0206 | 600/219 |
| 2007/0213596 A1 * | 9/2007 | Hamada | A61B 17/02 | 600/219 |
| 2015/0025324 A1 * | 1/2015 | Wan | A61B 1/32 | 600/245 |
| 2017/0273550 A1 * | 9/2017 | Wu | A61B 1/32 | |

* cited by examiner

EXPANDER

CROSS-REFERENCE TO RELATED APPLICATION

This non-provisional application claims priority under 35 U.S.C. § 119(a) to Patent Application No. 105109770 filed in Taiwan, R.O.C. on Mar. 28, 2016, the entire contents of which are hereby incorporated by reference.

BACKGROUND

Technical Field

The instant disclosure relates to an expander, in particular, to an expander for diagnosing use and rehabilitation.

Related Art

For pediatrics, stomatology, dentistry, gynecology and obstetrics, urology, etc., a tongue depressor or an expander are used commonly for expanding a flesh cavity for examination and diagnosis. Especially, in the treatment of stomatology and gynecology and obstetrics, expanders are commonly utilized as diagnostic tools. In addition, for a patient who has tumor in their head and neck and requires rehabilitation, or for a long-term bedridden patient, expanders are also commonly utilized as physical therapy tools or as tools aiding cleaning.

A common conventional expander is a clamp structure including two supporting member and an elastic pivoting member pivoted with the two supporting members. A user may press or hold the supporting member to increase the angle between the two supporting members to expand the cavity. However, the operation of the conventional expander takes effort, and the angle between the two supporting members cannot be maintained easily. A modified expander has a handle designed as the handle of a scissor or a plier. Although the operation of the modified expander takes less effort, the operation of the expander is quite different to, or even the opposite of, the operation of a scissor or a plier. As a result, the modified expander is not designed in an ergonomic way.

Additionally, the rehabilitation reports of a patient requiring rehabilitation must be recorded continuously as an evaluation reference for treatment. However, conventional expanders lack a function for measuring the expanding angle of the cavity. As a result, the conventional expanders cannot record the expanding angle of the cavity. Additionally, in stomatology, when a conventional expander is operated to expand the mouth of a patent, both the upper jaw and the lower jaw of the patient are forced by the expander, so that the patient may feel considerate discomfort, and the discomfort may further reduce the motivation of the patient for doing the rehabilitation.

SUMMARY

In view of these, in one embodiment, an expander is provided. The expander can be operated in an ergonomic way. The expanding angle of the expander may be measured. When the expander is operated, the patient's discomfort can be reduced. The expander can be applied to cavity examination and diagnosis in stomatology, dentistry, gynecology and obstetrics, urology, etc. In addition, the expander may be used for oral hygiene or the oral rehabilitation of a long-term bedridden patient.

In one embodiment, the expander comprises a first handle, a second handle, a first supporting member, and a second supporting member. The first handle is a fixed member and comprises a first gripping portion, a first pivoting portion, a first connecting portion, and an expanding compass. One of two ends of the first pivoting portion is connected to the first gripping portion, and the first connecting portion is extending from the other end of the first pivoting portion. The first gripping portion and the first connecting portion are substantially extending along the same direction. The expanding compass is extending from the first gripping portion. The second handle is a movable member and comprises a second gripping portion, a second pivoting portion, and a second connecting portion. The second gripping portion comprises a thru groove corresponding to the expanding compass, so that the expanding compass is inserted into the thru groove. The second pivoting portion is pivoted to the first pivoting portion. The second gripping portion is extending from one of two ends of the second pivoting portion, the second connecting portion is extending from the other end of the second pivoting portion, and an extension direction of the second connecting portion is not parallel to an extension direction of the second gripping portion. The first supporting member is connected to the first connecting portion. The second supporting member is connected to the second connecting portion. When the second gripping portion is moved toward the first gripping portion along the expanding compass, the second gripping portion drives the second supporting member to move away from the first supporting member.

In one embodiment, a shape of the first supporting member and a shape of the second supporting member are mirrored with each other.

In one embodiment, the expander further comprises an angle positioning member. The angle positioning member comprises an abutting portion and a pressing portion. The abutting portion is extending from the pressing portion and pivoted to two pivoting blocks at a wall of the thru groove. When the pressing portion is moved to drive the abutting portion abutting against the expanding compass, an angle between the first supporting member and the second supporting member is maintained. In addition, the expanding compass comprises a plurality of first tooth portions, and the abutting portion comprises a plurality of second tooth portions. The second tooth portions correspond to the first tooth portions. When the abutting portion is abutted against the expanding compass, protruded portions and recessed portions of parts of the second tooth portions are respectively engaged with recessed portions and protruded portions of the corresponding parts of the first tooth portions.

In one embodiment, the expander further comprises a light emitting module. The light emitting module comprises an LED and a button assembly. The LED is assembled on the first pivoting portion, protruded from a surface of the first pivoting portion, and between the first connecting portion and the second connecting portion. The button assembly is assembled in a through hole of the first pivoting portion, and the button assembly is electrically connected to the LED. In general, when the button assembly is not pressed, the button assembly is protruded from the first pivoting portion; while when the button assembly is pressed, the button assembly is partly recessed, and the LED emits light. Therefore, the expander may further provide an illumination function for inspection.

In one embodiment, the first pivoting portion is a sleeve having circular cross section, the second pivoting portion is a ring fitted over the first pivoting portion. Additionally, the expander further comprises a cap assembled on the second pivoting portion, and the cap covers one side of the second pivoting portion, wherein the side of the second pivoting portion is distal to the first pivoting portion.

In one embodiment, the first connecting portion comprises a first positioning shaft, and the second connecting portion comprises a second positioning shaft. The first supporting member comprises a first via hole, and the second supporting member comprises a second via hole. The first positioning shaft passes through the first via hole, and the first positioning shaft is engaged with the first supporting member. The second positioning shaft passes through the second hole, and the second positioning shaft is engaged with the second supporting member. Additionally, an end portion of the first positioning shaft comprises a first engaging section, and an end portion of the second positioning shaft comprises a second engaging section. A size of the first engaging section is bigger than a size of other portion of the first positioning shaft and a shape of the first engaging section corresponds to a shape of the first via hole. A size of the second engaging section is bigger than a size of other portion of the second positioning shaft and a shape of the second engaging portion corresponds to a shape of the second via hole. Additionally, when the first engaging section passes through the first via hole and the second engaging section passes through the second via hole, the first supporting member and the second supporting member are respectively rotated about the first positioning shaft and the second positioning shaft by an angle and positioned.

As above, an expander is provided. A user can press, with one finger, the second handle to move the second supporting member away from the first supporting member in an ergonomic way. The one directional expansion of the cavity may reduce the patient's discomfort. In addition, the expanding angle of the expander may be further measured, so the rehabilitation condition of a patient can be monitored chronically.

BRIEF DESCRIPTION OF THE DRAWINGS

The disclosure will become more fully understood from the detailed description given herein below for illustration only, and thus not limitative of the disclosure, wherein.

DETAILED DESCRIPTION

Figure 1:
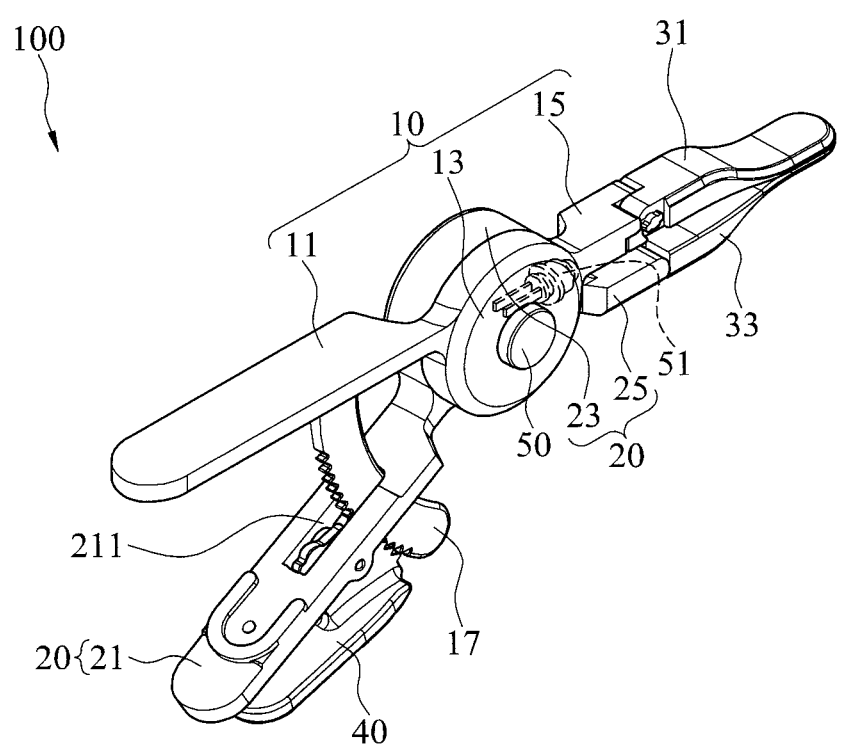
FIG. 1 illustrates a perspective view of an expander according an exemplary embodiment of the instant disclosure.
Figure 2:
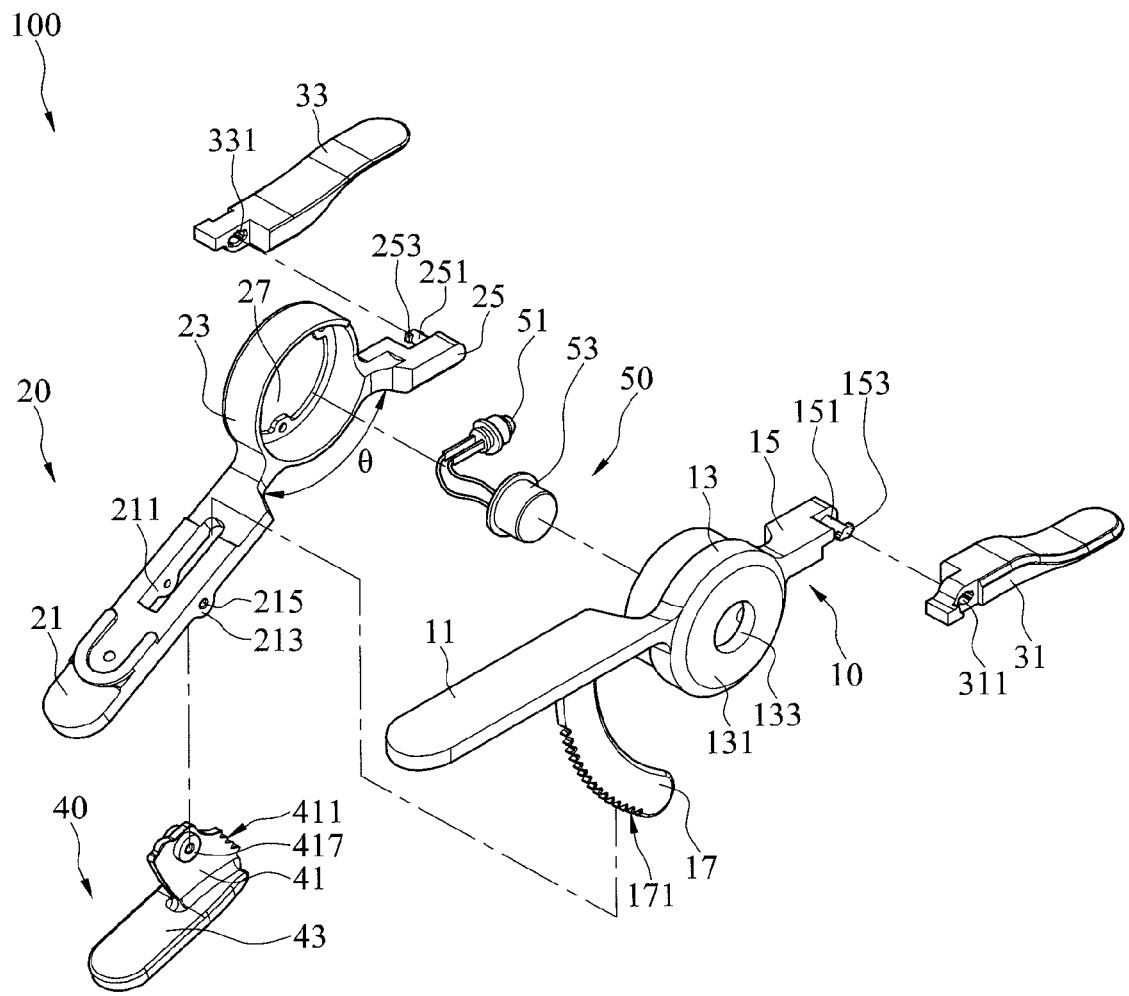
FIG. 2 illustrates an exploded view of the expander.

Please refer to FIGS. 1 and 2, respectively illustrating a perspective view and an exploded view of an expander 100 according to an exemplary embodiment of the instant disclosure. As shown in FIGS. 1 and 2, the expander 100 comprises a first handle 10, a second handle 20, a first supporting member 31, and a second supporting member 33. In this embodiment, the first handle 10 is a fixed member, the second handle 20 is a movable member, and the first handle 10 is connected to the second handle 20. The first supporting member 31 and the second supporting member 33 are respectively connected to the first handle 10 and the second handle 20.

The first handle 10 comprises a first gripping portion 11, a first pivoting portion 13, a first connecting portion 15, and an expanding compass 17. The first pivoting portion 13 is a sleeve substantially having circular cross section. One of two ends of the first pivoting portion 13 is connected to the first gripping portion 11, and the first connecting portion 15 is extending from the other end of the first pivoting portion 13. The extension direction of the first gripping portion 11 and the extension direction of the first connecting portion 15 are substantially parallel with each other. The expanding compass 17 is extending from the first gripping portion 11 and may be a curved bar structure. The structure of the expanding compass 17 illustrated herein is as an illustrative purpose, but not a limitation. A surface of the expanding compass 17 comprises a plurality of first tooth portions 171. The expanding compass 17 further has scales indicating a different expanding extent, so that the expanding angle of a cavity can be measured directly.

The second handle 20 comprises a second gripping portion 21, a second pivoting portion 22, and a second connecting portion 25. The second gripping portion 21 comprises a thru groove 211 corresponding to the expanding compass 17, so that the expanding compass 17 is inserted into the thru groove 211. The second pivoting portion 23 may be a ring fitted over the first pivoting portion 13. The second gripping portion 21 is extending from one of two ends of the second pivoting portion 23, the second connecting portion 25 is extending from the other end of the second pivoting portion 23, and the extension direction of the second connecting portion 25 is not parallel to the extension direction of the second gripping portion 21. For example, as shown in FIG. 2, a fixed angle θ is formed between the second connecting portion 25 and the second gripping portion 21. In this embodiment, the fixed angle θ is approximately 130 degrees, but embodiments are not limited thereto. The fixed angle θ may be between 0 degree and 180 degrees, and in some embodiments, the fixed angle θ may be greater than or equal to 60 degrees but less than or equal to 150 degrees. The first supporting member 31 is connected to the first connecting member 15, and the second supporting member 33 is connected to the second connecting member 25. The shape of the first supporting member 31 is mirrored to the shape of the second supporting member 33. For example, the first supporting member 31 and the second supporting member 33 may be formed as a duckbill-like structure. In other words, the thickness of the end portion of the first supporting member 31 (or the second supporting member 33), is less than the thickness of the body portion of the first supporting member 31 (or the second supporting member 33).

Figure 3:
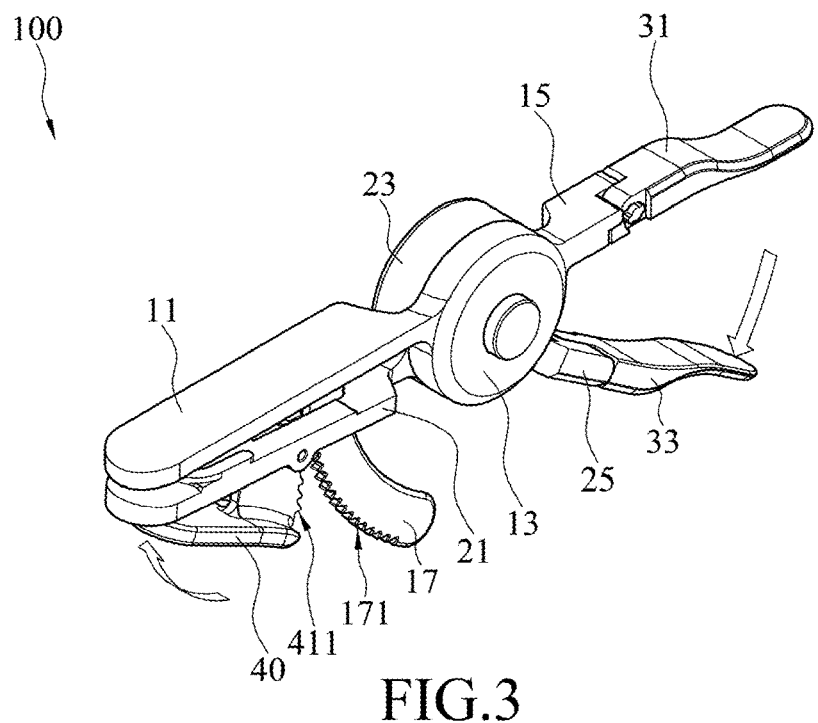
FIG. 3 illustrates a schematic perspective view showing that the expander is in an operable state.

FIG. 3 illustrates a schematic perspective view showing that the expander 100 is in an operable state. Please refer to FIGS. 1 and 3, in which when the second gripping portion 21 is forced to move toward the first gripping portion 11 along the expanding compass 17, the second supporting member 33 is moved away from the first supporting member 31, so that the angle between the first supporting member 31 and the second supporting member 33 increases, and a cavity operated by the expander 100 can be expanded as well. In this embodiment, during the operation of the expander 100, the second handle 20 drives the movement of the second supporting member 33, so that the cavity is expanded in one direction.

Figure 4:
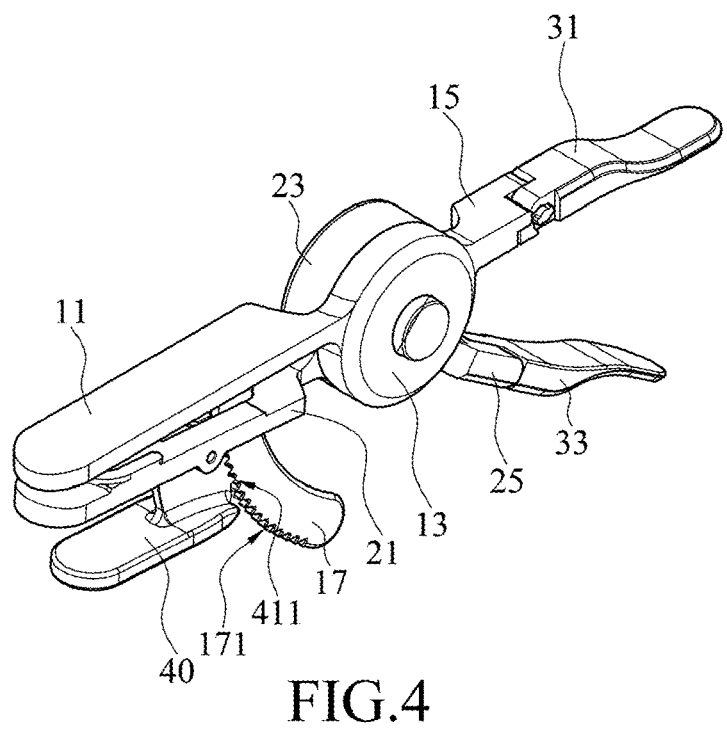
FIG. 4 illustrates a schematic perspective view showing that the expander is in a fixed state.

FIG. 4 illustrates a schematic perspective view showing that the expander 100 is in a fixed state. Please refer to FIGS. 2 to 4, in which the expander 100 further comprises an angle positioning member 40. The angle positioning member 40 comprises an abutting portion 41 and a pressing portion 43. The abutting portion 41 is extending from the pressing portion 43 and not parallel to the pressing portion 43. The abutting portion 41 is pivoted to two pivoting blocks 213 at the wall of the thru groove 211. For example, the abutting portion 41 may comprise a shaft 417 passing through pivoting holes 215 of the two pivoting blocks 213, and thus the abutting portion 41 is rotatable about the pivoting blocks 213. When the pressing portion 43 is forced to drive the abutting portion 41 to abut against the expanding compass 17, the angle between the first gripping portion 11 and the second gripping portion 21 can be maintained, so that the angle between the first supporting member 31 and the second supporting member 33 can be maintained.

Figure 5:
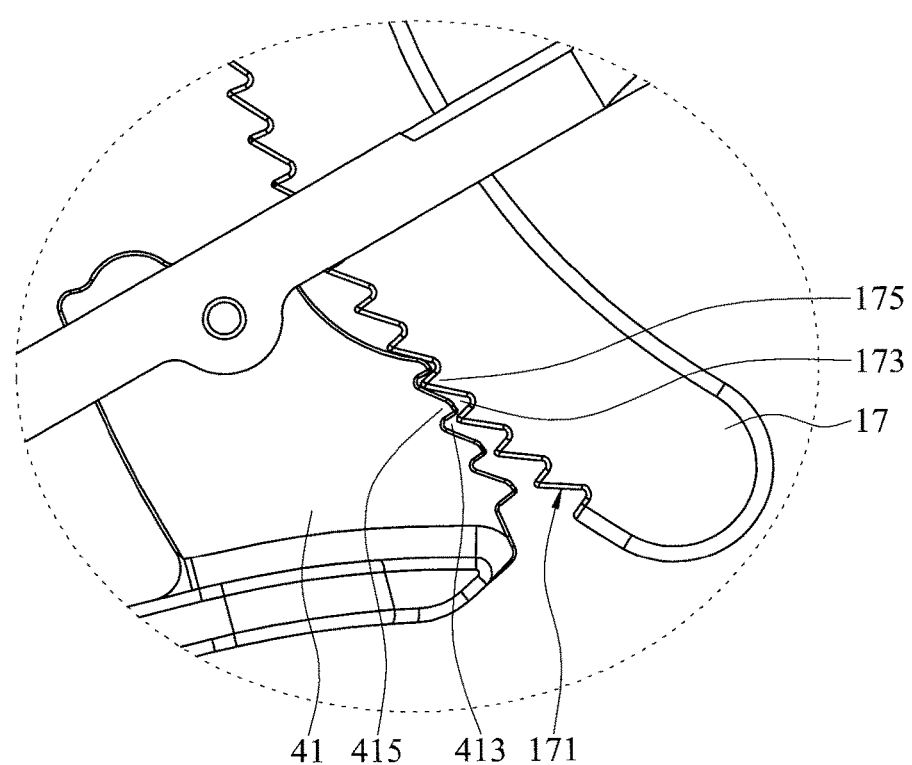
FIG. 5 illustrates a partial enlarged view showing that the expander is in the fixed state.

FIG. 5 illustrates a partial enlarged view showing that the expander 100 is in the fixed state, and FIG. 5 is a partial enlarged view of FIG. 4. Please refer to FIGS. 4 and 5, in which the abutting portion 41 further comprises a plurality of second tooth portions 411. When the abutting portion 41 is abutted against the expanding compass 17, protruded portions 415 and recessed portions 413 of parts of the second tooth portions 411 are respectively engaged with recessed portions 173 and protruded portions 175 of the corresponding parts of the first tooth portions 171, so that the first handle 10 and the second handle 20 are positioned with each other. When a user tends to adjust the expanding angle of the expander 100, he or she presses the pressing portion 43 to drive the abutting portion 41 to move away from the expanding compass 17 and return to a state illustrated in FIG. 3. Accordingly, the second handle 20 can move along the expanding compass 17 again.

Please refer to FIGS. 1 and 2, in which the expander 100 further comprises a light emitting module 50. The light emitting module 50 comprises a LED 61 and a button assembly 53. The LED 51 is assembled on the first pivoting portion 13, protruded from the outer surface of the first pivoting portion 13, and between the first connecting portion 15 and the second connecting portion 25. The button assembly 53 is assembled in a through hole 133 of a side surface 131 of the first pivoting portion 13. The button assembly 53 is electrically connected to the LED 51. Normally, the button assembly 53 may be a pressable switch comprising a battery therein (not shown). When the button assembly 53 is not pressed, the button assembly 53 is protruded from the side surface 131 of the first pivoting portion 13. While when the button assembly 53 is pressed, the battery is electrically connected to the LED 51 to allow the LED 51 emitting light. Accordingly, when a gynecologic doctor or a dentist examines a patient's cavity, light emitted from the LED 51 can provide a function of illumination. In addition, the light emitted from the LED 51 can be further reflected by a lens for inspecting the cavity clearly. In addition, the expander 100 may further comprise a cap 27 assembled on the second pivoting portion 23. The cap 27 covers one side of the second pivoting portion 23, wherein the side of he second pivoting portion 23 is distal to the first pivoting portion 13. Accordingly, the button assembly 53 can be shielded by the cap 27, and when being impacted by an external force, the button assembly 53 would not detach from the expander 100 or be damaged easily.

Figure 6A:
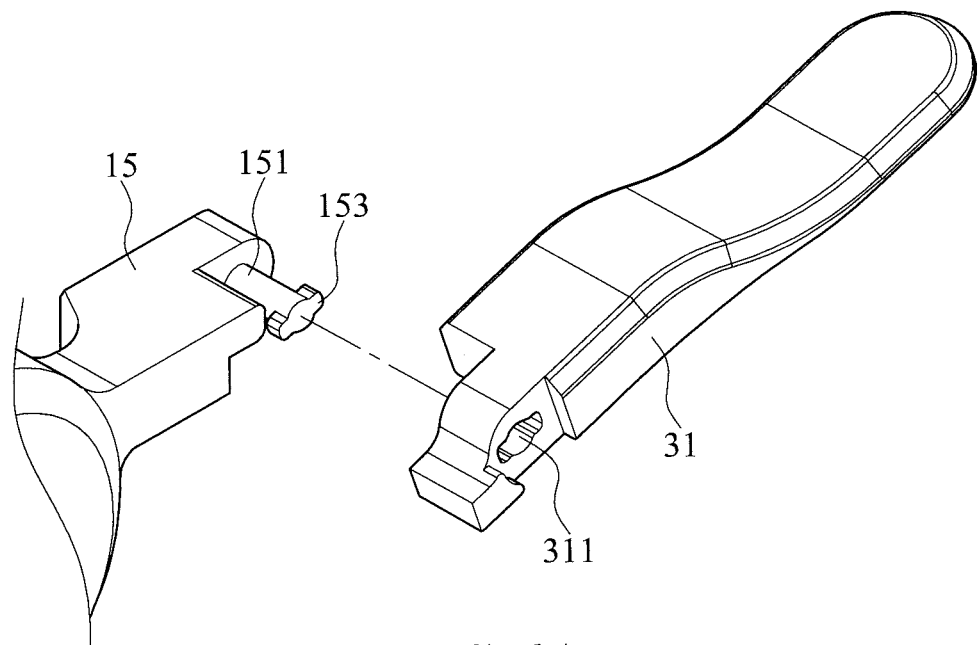
FIGS. 6A to 6C illustrate sequential partial perspective views showing the assembling of the expander.
Figure 6B:
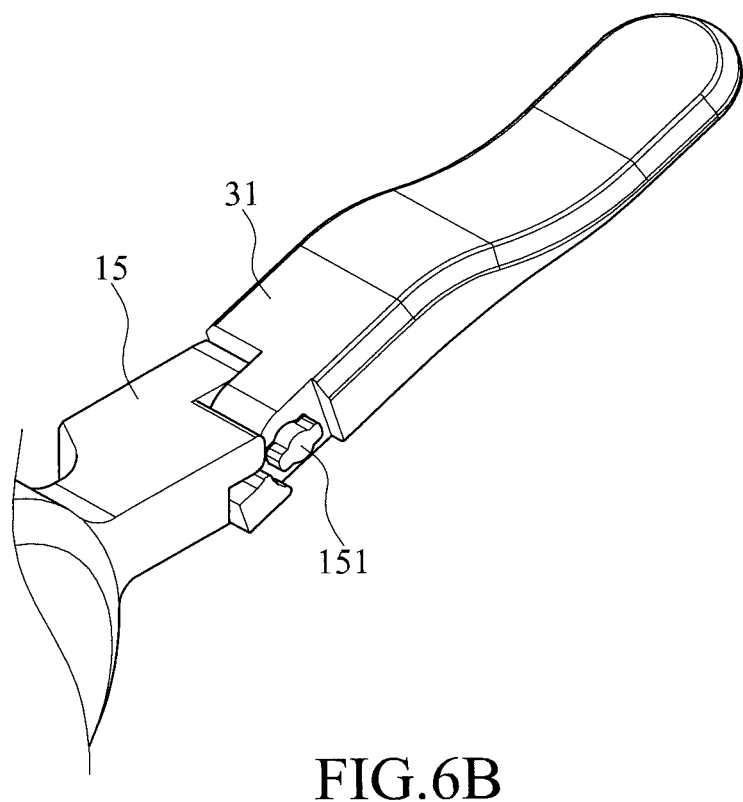
Figure 6C:
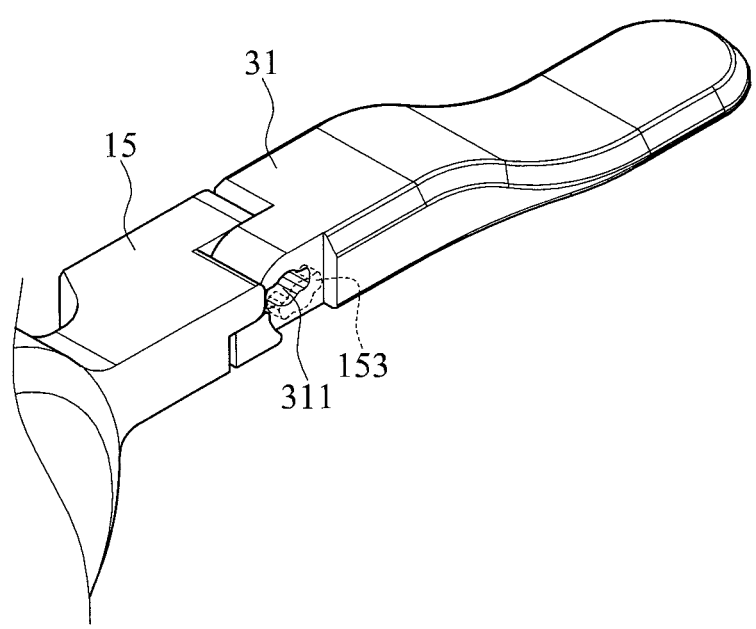

FIGS. 6A to 6C illustrate sequential partial perspective views showing the assembling of the expander 100. Please refer to FIGS. 2 and 6A to 6C, in which the first connecting portion 15 comprises a first positioning shaft 151. The second connecting portion 25 comprises a second positioning shaft 251. The first supporting member 31 comprises a first via hole 311. The second supporting member 33 comprises a second via hole 331. The first positioning shaft 151 corresponds to the first via hole 311. After the first positioning shaft 151 passes through the first via hole 311, the first positioning shaft 151 is engaged with the first supporting member 31. The second positioning shaft 251 corresponds to the second via hole 331. After the second positioning shaft 251 passes through the second via hole 331, the second positioning shaft 251 is engaged with the second supporting member 33. As shown in FIGS. 5 and 6A to 6C, an end portion of the first positioning shaft 151 comprises a first engaging section 153, and an end portion of the second positioning shaft 251 comprises a second engaging section 253. The size of the first engaging section 153 is bigger than the size of other portion of the first positioning shaft 151, and the shape of the first engaging section 153 corresponds to the shape of the first via hole 311. The size of the second engaging section 253 is bigger than the size of other portion of the second positioning shaft 251, and the shape of the second engaging section 253 corresponds to the shape of the second via hole 331.

As shown in FIG. 6A, each of the first engaging portion 153 and the second engaging portion 253 has a neck that has a thinner width (as compared with other portion of the engaging portion). The first via hole 311 and the second via hole 331 respectively correspond to the first engaging section 153 and the second engaging section 253, so that the first engaging section 153 can pass through the first via hole 311, and the second engaging section 253 can pass through the second via hole 331. As shown in FIG. 6B, the first engaging section 153 passes through the first via hole 311, and the second engaging section 253 passes through the second via hole 331. Lastly, as shown in FIG. 6C, the first supporting member 31 is rotated about the first positioning shaft 151 by an angle, and the second supporting member 33 is rotated about the second positioning shaft 251 by the same angle (it is understood that the second supporting member 33 may be rotated about the second positioning shaft 251 by a different angle). Therefore, the first engaging section 153 is engaged with the side surface of a portion of the first supporting member 31 having the first via hole 311, and the second engaging section 253 is engaged with the side surface of a portion of the second supporting member 33 having the second via hole 331, so that the first connecting portion 15 is positioned with the first supporting member 31 and the second connecting portion 25 is positioned with the second supporting member 33. After the first connecting portion 15 is engaged with the first supporting member 31 and the second connecting portion 25 is engaged with the second supporting member 33, the extension direction of the first supporting member 31 is approximately parallel with the extension direction of the first connecting portion 15, and the extension direction of the second supporting member 33 is approximately parallel with the extension direction of the second connecting portion 25. Consequently, the first supporting member 31 and the second supporting member 33 can be quick release structures, and the first supporting member 31 and the second supporting member 33 with different shapes can be replaced quickly for different cavities.

Additionally, the first supporting member 31 and the second supporting member 33 may be made of aluminum alloy, titanium alloy, or anodized metal or alloy. Accordingly, the first supporting member 31 and the second supporting member 33 can be sterilized under a high temperature and high pressure condition and can be used repeatedly.

As above, an expander is provided. A user can press, with one finger, the second handle to move the second supporting member away from the first supporting member in an ergonomic way. The one directional expansion of the cavity may reduce the patient's discomfort. In addition, the expanding angle of the expander may be further measured, so the rehabilitation condition of a patient can be monitored chronically.

While the disclosure has been described by the way of example and in terms of the preferred embodiments, it is to be understood that the invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. An expander, comprising:
a first handle, comprising a first gripping portion, a first pivoting portion, a first connecting portion, and an expanding compass, wherein one of two ends of the first pivoting portion is connected to the first gripping portion, and the first connecting portion is extending from the other end of the first pivoting portion, the expanding compass is extending from the first gripping portion;
a second handle, comprising a second gripping portion, a second pivoting portion, and a second connecting portion, wherein the second gripping portion comprises a thru groove corresponding to the expanding compass, so that the expanding compass is inserted into the thru groove, the second pivoting portion is pivoted to the first pivoting portion, wherein the second gripping portion is extending from one of two ends of the second pivoting portion, the second connecting portion is extending from the other end of the second pivoting portion, and an extension direction of the second connecting portion is not parallel to an extension direction of the second gripping portion;
a first supporting member connected to the first connecting portion; and
a second supporting member connected to the second connecting portion;
wherein when the second gripping portion is moved toward the first gripping portion along the expanding compass, the second gripping portion drives the second supporting member to move away from the first supporting member.

2. The expander according to claim 1, further comprising an angle positioning member, wherein the angle positioning member comprises an abutting portion and a pressing portion, the abutting portion is extending from the pressing portion and pivoted to two pivoting blocks at a wall of the thru groove, wherein when the pressing portion is moved to drive the abutting portion abutting against the expanding compass, an angle between the first supporting member and the second supporting member is maintained.

3. The expander according to claim 2, wherein the expanding compass comprises a plurality of first tooth portions, and the abutting portion comprises a plurality of second tooth portions corresponding to the first tooth portions, wherein when the abutting portion is abutted against the expanding compass, protruded portions and recessed portions of parts of the second tooth portions are respectively engaged with recessed portions and protruded portions of the corresponding parts of the first tooth portions.

4. The expander according to claim 1, further comprising a light emitting module, wherein the light emitting module comprises an LED and a button assembly, the LED is assembled on the first pivoting portion, protruded from a surface of the first pivoting portion, and between the first connecting portion and the second connecting portion, the button assembly is assembled in a through hole of the first pivoting portion, and the button assembly is electrically connected to the LED.

5. The expander according to claim 1, wherein the first pivoting portion is a sleeve, and the second pivoting portion is a ring fitted over the first pivoting portion.

6. The expander according to claim 5, further comprising a cap assembled on the second pivoting portion, the cap covers one side of the second pivoting portion, wherein the side of the second pivoting portion is distal to the first pivoting portion.

7. The expander according to claim 1, wherein a shape of the first supporting member and a shape of the second supporting member are mirrored with each other.

8. The expander according to claim 1, wherein the first connecting portion comprises a first positioning shaft, the second connecting portion comprises a second positioning shaft, the first supporting member comprises a first via hole, the second supporting member comprises a second via hole, the first positioning shaft passes through the first via hole and engaged with the first supporting member, the second positioning shaft passes through the second hole and engaged with the second supporting member.

9. The expander according to claim 8, wherein an end portion of the first positioning shaft comprises a first engaging section, an end portion of the second positioning shaft comprises a second engaging section, a size of the first engaging section is bigger than a size of other portion of the first positioning shaft and a shape of the first engaging section corresponds to a shape of the first via hole, a size of the second engaging section is bigger than a size of other portion of the second positioning shaft and a shape of the second engaging portion corresponds to a shape of the second via hole.

10. The expander according to claim 9, wherein when the first engaging section passes through the first via hole and the second engaging section passes through the second via hole, the first supporting member and the second supporting member are respectively rotated about the first positioning shaft and the second positioning shaft by an angle and positioned.

* * * * *